(12) United States Patent
Howard et al.

(10) Patent No.: US 6,642,277 B1
(45) Date of Patent: *Nov. 4, 2003

(54) FOOD SUPPLEMENTS CONTAINING POLYPHENOLS

(75) Inventors: Alan Norman Howard, Cambridge (GB); Shaja Vijay Nigdikar, Suffolk (GB); Jayshri Rajput-Williams, Cambridge (GB); Norman Ross Williams, Cambridge (GB)

(73) Assignee: The Howard Foundation, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/488,642

(22) Filed: Jan. 21, 2000

Related U.S. Application Data

(63) Continuation-in-part of application No. 08/978,158, filed on Nov. 25, 1997, now Pat. No. 6,086,910, which is a continuation-in-part of application No. 08/934,055, filed on Sep. 19, 1997, now Pat. No. 6,099,854.

(30) Foreign Application Priority Data

Sep. 20, 1996 (GB) ............................................. 9619700
May 31, 1997 (GB) ............................................. 9711171
May 31, 1997 (GB) ............................................. 9711172
May 31, 1997 (GB) ............................................. 9711173

(51) Int. Cl.⁷ ............................. A61P 7/02; A61P 9/10; A61K 31/05; A61K 31/353; A61K 35/78
(52) U.S. Cl. ........................ 514/783; 514/456; 514/577; 514/824; 424/439; 424/195.1
(58) Field of Search ................................ 514/824, 783, 514/456, 577; 424/439, 195.1

(56) References Cited

U.S. PATENT DOCUMENTS 6,086,910 A * 7/2000 Howard et al.

\* cited by examiner

Primary Examiner—Edward J. Webman
(74) Attorney, Agent, or Firm—Piper Rudnick LLP; Perry E. Van Over

(57) ABSTRACT

Disclosed is a plant-derived flavonol-containing dry composition suitable for human consumption, wherein at least 25% of the plant-derived material in the composition comprises polyphenols, together with uses thereof.

44 Claims, 2 Drawing Sheets

FOOD SUPPLEMENTS CONTAINING POLYPHENOLS

This is a Continuation-in-Part of application Ser. No. 08/978,158, now U.S. Pat. No. 6,086,910 filled Nov. 25, 1997, which is a continuation-in-part of Ser. No. 08/954,055 filled Sep. 19, 1997, now U.S. Pat. No. 6,099,854.

FIELD OF THE INVENTION

This invention relates to, inter alia, to certain compositions, uses thereof, and to food supplements and drinks for human consumption containing the compositions.

BACKGROUND OF THE INVENTION

The high consumption of wine in France is thought to be an important dietary factor in the low incidence of coronary heart disease (CHD) mortality and has been suggested at least in part to provide a possible explanation for the phenomenon known as the "French Paradox" (Renaud & De Lorgeril 1992), France being an exception compared with most other countries because CHD mortality is low despite a high intake of saturated fat.

There is a considerable literature on the alleged beneficial effects of red wine in relation to prevention of coronary heart disease (CHD). Epidemiological data suggest the protection afforded by wine is superior to that of other alcoholic beverages such as beer and spirits, indicating that factors other than alcohol content in wine is contributing to the effect (St Leger et al., 1979; Renaud & De Lorgeril 1992). In a prospective study in Copenhagen, Denmark various parameters (including alcohol intake, smoking habit and body mass index) were assessed in 13,285 people succeeded by a 12 year follow-up of mortality. It was shown that low to moderate intake of wine (but not beer or spirits) was associated with lower mortality from cardiovascular and cerebrovascular diseases and other causes (Gronbaek et al., 1995). These results confirmed those previously reported in the USA (Klatsky & Armstrong, 1993).

There is growing evidence that the free radical chain reaction of lipid peroxidation involving the oxidation of low density lipoproteins (LDL) plays an important contributory role in the development of atherosclerosis and CHD (Steinberg, 1993).

Frankel et al (1993) examined the ability of dilute, dealcoholised red wine to inhibit the oxidation of human LDL in vitro, and found the wine to be very active as an antioxidant. The authors suggested that the routine consumption of red wine may "reduce oxidation of lipoproteins and reduce thrombotic phenomena". However, the authors admitted that "we need to know more about the pharmaco-kinetics of wine flavonoids and the absorption and metabolism of wine phenols . . . if we are to evaluate further the potential role of antioxidant compounds in red wine in reducing CHD".

Polyphenols are those compounds which include more than one phenolic group. Polyphenols occur abundantly in red wine and consist of a large number of different chemical substances of varying molecular weights. The chief polyphenol components of grapes and wine, and their concentrations, are described by Shahidi & Nazck (1995). Among the polyphenols are the following classes: flavonoids (a term often used to denote polyphenols in general, but more commonly in Europe to denote only the flavones), the flavanols, proanthocyanidins (also called procyanidols, procyanins, procyanidins and tannins) and anthocyanins.

The flavones are compounds with a basic structure shown in FIG. 1 in which two benzene rings (A and B) are linked with a heterocyclic six member ring C containing a carbonyl group. Ring B can be joined in position 2 (as illustrated) to give a flavone or to position 3 to give an iso flavone. Hydroxylation can occur at positions 3, 5, 7 and 3', 4', 5' to give compounds called flavonols. Typical examples of flavonols are: quercetin, (hydroxylated at positions 3, 5, 7, 3', 4'), kaempferol (hydroxylated at positions 3, 5, 7, 4'), and myricetin (hydroxylated at positions 3, 5, 7, 3', 4', 5'). They can exist naturally as the aglycone or as O-glycosides (e.g. D-glucose, galactose, arabinose, rhamnose etc). Other forms of substitution such as methylation, sulphation and malonylation are also found.

The flavanols have a basic structure shown in FIG. 2. The two most common flavanols are catechin (hydroxyl groups positions 5, 7, 3', 4') and its stereo-isomer epi-catechin. The hydroxyl groups can be esterified with gallic acid (shown in FIG. 3). The proanthocyanidins are polymers of catechin and/or epicatechin and can contain up to 8 units or more.

The anthocyanins are coloured substances with a basic structure shown in FIG. 4. They are sometimes called anthocyanidins. Typical examples are: cyanidin (hydroxylated at positions 3, 5, 7, 3', 4'), delphinidin (hydroxylated at positions 3, 5, 7, 3', 4', 5') and pelargonidin (hydroxylated at positions 3, 5, 7, 3'). The hydroxyl groups are usually glycosylated and/or methoxylated (e.g. malvidin at 3', 5').

Within the general term "polyphenols" are included the dihydroxy- or tri-hydroxy benzoic acids and the phytoalexins, a typical example of which is resveratrol (shown in FIG. 5).

The most widely used method for the determination of LDL oxidation is to employ the transition metal copper (specifically $Cu^{2+}$ ions) as a catalyst to promote the oxidation of endogenous lipid hydroperoxides. Antioxidants present in LDL, especially alpha tocopherol, delay the oxidation process and produce a so called lag phase. The process can be easily followed in a UV spectrophotometer because the oxidation reaction produces conjugated dienes which can be continuously monitored at 234 nm (Esterbauer et al., 1989). To preserve LDL from oxidation during storage, EDTA is added to complex copper and other trace elements. This excess EDTA interferes with the copper catalysed oxidation. EDTA can be removed by dialysing the LDL preparation before addition of the copper ions or an excess of copper ions can be added to compensate for those complexed with EDTA.

The results of in vitro experiments somewhat similar to those described by Frankel et al., (Lancet 1993, cited above) were also reported by Frankel et al. (1995). The authors of this publication draw attention to the difficulty of interpreting in vitro data. Thus "Although the phenolic compounds have similar chemical properties, their reducing capacity is not a very precise predictor of their antioxidant activity. In the LDL oxidation assay and other tests for antioxidant activity, the system is typically heterogeneous and physical properties, such as lipophilicity, solubility and partition between the aqueous and lipid phases of LDL can become important in determining antioxidant activity".

Indeed, those skilled in the art appreciate that extrapolation from in vitro findings to in vivo situations is frequently inappropriate. As an example, the reader is referred to the publication of McLoone et al, (1995), which shows that although the compound lutein has the potential to inhibit LDL oxidation in vitro, supplementation of the diet of human volunteers with lutein for 2 weeks (which gave a 6-fold increase in the levels of lutein in plasma) had no effect on LDL oxidation.

Some in vivo trials have been conducted to investigate the possible health benefits of red wine. Fuhrman et al., (1995) found that "some phenolic substances that exist in red wine, but not in white wine, are absorbed, bind to plasma LDL, and may be responsible for the antioxidant properties of red wine" and provided, in their words, the first demonstration "that red wine consumption inhibits the propensity of LDL to undergo lipid peroxidation", and that this may contribute to attenuation of atherosclerosis. However, a study by Sharpe et al, (1995) nearly contemporaneously with those of Fuhrman et al, found that neither consumption of red wine nor white wine had any effect "on total cholesterol, triglycerides, HDL or measures of antioxidant status, including the susceptibility of LDL to oxidation".

De Rijke et al. (1996) also investigated the matter and conducted a randomized double-blind trial. They stated that "The results of this study do not show a beneficial effect of red wine consumption on LDL oxidation".

Thus, to summarise, there are several reports that dilute red wine can inhibit LDL oxidation in in vitro assays, but that these findings cannot necessarily be extended to the in vivo situation. Further, the in vivo data relating to inhibition of LDL oxidation by red wine consumption are at best conflicting and there is no clear evidence to suggest that red wine consumption has any effect on LDL oxidation.

A number of compositions are now publicly available which are prepared from wine or grape by-products and which may contain polyphenols (albeit at quite low levels in some of the compositions). Among these are French Paradox™ capsules (available from Arkopharma). French Paradox™ capsules are made by preparing an extract from marc (the grape skin waste remaining after wine fermentation). Most of the polyphenols present in the grape skins are alcohol-soluble, and so tend to be extracted into the fermenting wine. Hence, French Paradox™ capsules have actually rather low polyphenol content. (Other publicly available compositions include an anthocyanin-containing powder (obtainable from Sefcal™) made from a grape skin extract, and which is used as a food colourant, and a proanthocyanidin-containing composition (Endotelon™) prepared from grape seeds.)

Even if French Paradox™ capsules contained significant amounts of polyphenols, it is not clear that oral consumption of such a synthetic polyphenol composition would exert the same therapeutic effect allegedly associated with red wine consumption. For example, as explained by Goldberg (1995) the alcohol content of wine keeps polyphenols in solution in wine and in the human intestine, such that they might be available for absorption. A synthetic, alcohol-free polyphenol powder may be completely ineffective because the polyphenols are insufficiently soluble in the intestine (in the absence of alcohol) to be absorbed. Additionally, absorption into the bloodstream may not be sufficient for any antioxidant effect to be exerted on LDL—intimate association of the polyphenols with the LDL fraction may be required.

It is recognised that many diseases are caused or provoked by a free radical oxidation mechanism e.g. cancer, cataracts, diabetes etc. Antioxidant nutrients such as vitamin E, vitamin C and others are thought to prevent free radical oxidation in many organs and tissues. Thus the absorption of polyphenols which are effective antioxidants are likely to have an effect on free radical/oxidation diseases in general, and the use of polyphenols may be much wider than a treatment or prevention of coronary heart disease.

Nevertheless, CHD is one of the major causes of mortality and morbidity in the western world, and therefore of particular interest. Pathogenesis of the condition consists essentially of a two stage process involving first the development of atherosclerotic plaques and then formation of a thrombus (clot) on the plaque (a process called thrombosis) which may cause arterial occlusion, the consequences of which can be myocardial infarction (MI) and sudden death. Other diseases which are caused by thrombosis are stroke and venous thrombosis. The initial stage in the formation of a thrombus is the aggregation of platelets which then release coagulation factors into the blood causing the production of fibrin clots.

Once the blood clots are formed they can be removed by a process known as fibrinolysis, which is essentially the dissolution of clots and the degradation of fibrin to degradation products. Thus there are at least two processes by which thrombosis can be prevented: inhibiting the aggregation of platelets, or increasing fibrinolysis.

Abnormal vascular smooth muscle cell (VSMC) proliferation may contribute to the formation of obstructive lesions in coronary heart disease, atherosclerosis, restenosis, stroke and smooth muscle neoplasms of the bowel and uterus, uterine fibroid or fibroma.

It has been known for many years that TGF-$\beta$ is one of the most potent cell growth inhibitors (Massague, 1990), and several authors have found that TGF-$\beta$ inhibits VSMC proliferation (Assolian, 1986; Bjorkerud, 1991; Owens, 1988; Kirschenlohr, 1993). Human VSMC produce TGF-$\beta$ in a latent, inactive form which is activated proteolytically by the serine protein plasmin, which in turn is obtained from plasminogen by a family of plasminogen activators (PAs), such as tissue plasminogen activator (tPA) (Lyons, 1990). An increase in total plasma TGF-$\beta$ is considered effective in inhibiting the growth of VSMC, since the latent form is converted into the active form by plasmin.

Several authors have developed methods for the estimation of the plasma level of TGF-$\beta$ and to search for pharmaceutical compounds which may stimulate TGF-$\beta$ production both in the latent and active form. In U.S. Pat. No. 5,545,569 (Grainger et al) a method is claimed for determining in vitro the effectiveness of compounds which increase the plasma level of TGF-$\beta$ and stimulate its production using the techniques described therein. W094/26303 (Grainger et al) discloses a method for maintaining or increasing the vessel lumen diameter in a diseased or injured vessel of a mammal by administering an effective amount of TGF-$\beta$ activator or production stimulator. The compound Tamoxifen (trans-2[4(diphenyl-1-butanyl)phenoxy]-dimethyl ethylamine is claimed as being effective, since it stimulates the production of TGF-$\beta$, and increases the ratio of active to latent TGF-$\beta$. Another compound showing activity is aspirin (Grainger, et al, 1995) which increases both total and active serum TGF-$\beta$ in normal people but only total TGF-$\beta$ in patients with coronary heart disease.

An increase in platelet aggregation has also been significantly associated with prevalence (Elwood et al, 1991) and incidence (Thaulou et al, 1991) of CHD. Platelet aggregation is conveniently studied using a platelet aggregometer in which a suspension of platelets freshly obtained from blood is placed in contact with an agonist which causes aggregation. Many agonists may be used but the most typical are arachidonic acid, ADP, collagen and thrombin. From a measurement of the maximum aggregation (%) it is possible to study the effects of the inhibitors of platelet aggregation which may be given orally or by injection to the subject. One of the most effective substances in preventing platelet aggregation is aspirin, which inhibits cyclo-oxygenase activity and formation of thromboxane, a necessary factor in thrombus formation (Moncada & Vane, 1979). Aspirin also prevents CHD, stroke and sudden death (Hennekens et al, 1988).

The fibrinolytic system constitutes a cascade of extracellular proteolytic reactions tightly regulated by activators and inhibitors. The enzyme tissue-type plasminogen activator (t-PA) converts plasminogen to plasmin, which in turn dissolves fibrin clots. t-PA is a glycoprotein synthesized in the endothelial cells, which is adsorbed on to fibrin in order to be activated. Plasminogen activator inhibitor (PAI)-1, is a serine protease inhibitor and acts as a specific inhibitor of t-PA. PAI-1 exists in three forms: active, latent, and as an inactive complex. It is synthesised in endothelial cells, liver and platelets.

In the circulation most tPA (95%) is complexed with PAI-1. Very little tPA and PAI-1 are in the free (active) form. A decreased fibrinolytic activity is thought to be due to an increase in PAI-1 level or activity, which results in decreased activation of plasminogen to plasmin by tPA. This is important because of reports of an association between decreased fibrinolytic activity and risk of CHD (Mehta et al, 1987) and MI. Impaired fibrinolysis, mainly due to elevation of plasma PAI-1, is a common finding in thrombotic disease. In the Northwick Park Heart Study, a prospective epidemiological study of middle aged men (40–54 at entry), Meade et al (1987) reported that a decreased fibrinolytic activity is a major independent risk factor for future CHD. Cross-sectional studies of patients with angina pectoris or previous myocardial infarction have consistently shown a decreased fibrinolytic activity in patients compared to control (Hamsten et al., 1985 and 1986; Johnson 1984; Paramo et al., 1985; Aznar et al., 1986; Francis 1988; and Olofson et al., 1989). PAI-1 concentrations have been shown to be higher in MI patients compared to controls (Hamsten et al., 1987).

Because of the role of platelet aggregation and fibrinolysis in the formation of thrombi, a method of decreasing platelet aggregation and/or increasing fibrinolysis could be employed as a method of treatment of thrombotic diseases in general, and CHD in particular.

SUMMARY OF THE INVENTION

The invention relates to a method of providing a therapeutic effect to a subject, the method including providing a flavonol and anthocyanin containing dry composition prepared from plant material selected from the group consisting of wine or grape juice, wherein the composition is water soluble and comprises at least 25% w/w polyphenols, the composition comprising at least 0.1% flavonol, and administering the composition to the subject in a therapeutically effective dosage.

The invention further relates to a method of providing a therapeutic effect in relation to the prevention or treatment of coronary heart disease in a subject, the method including providing a flavonol and anthocyanin containing dry composition prepared from plant material selected from the group consisting of wine or grape juice, wherein the composition is water soluble and comprises at least 25% w/w polyphenols, the composition comprising at least 0.1% flavonol, and administering the composition to the subject in a therapeutically effective dosage.

The invention also relates to a method of inhibiting oxidation of plasma LDL in a human subject, the method including providing a flavonol and anthocyanin containing dry composition prepared from plant material selected from the group consisting of wine or grape juice, wherein the composition is water soluble and comprises at least 25% w/w polyphenols, the composition comprising at least 0.1% flavonol, and administering the composition to the subject in a therapeutically effective dosage.

The invention also relates to a method of stimulating TGF-$\beta$ production in a human subject, the method including providing a flavonol and anthocyanin containing dry composition prepared from plant material selected from the group consisting of wine or grape juice, wherein the composition is water soluble and comprises at least 25% w/w polyphenols, the composition comprising at least 0.1% flavonol, and administering the composition to the subject in a therapeutically effective dosage.

The invention also relates to a method of inhibiting platelet aggregation or stimulating fibrinolysis in a human subject, the method including providing a flavonol and anthocyanin containing dry composition prepared from plant material selected from the group consisting of wine or grape juice, wherein the composition is water soluble and comprises at least 25% w/w polyphenols, the composition comprising at, least 0.1% flavonol, and administering the composition to the subject in a therapeutically effective dosage.

BRIEF DESCRIPTION OF THE DRAWINGS

The invention is further demonstrated by reference to the following figures, wherein.

DETAILED DESCRIPTION OF THE INVENTION

Figure 1:
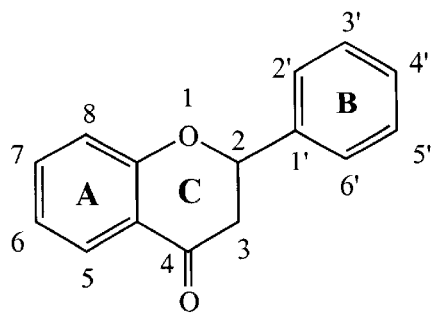
FIG. 1 is a schematic representation of the core structure of flavones.
Figure 2:
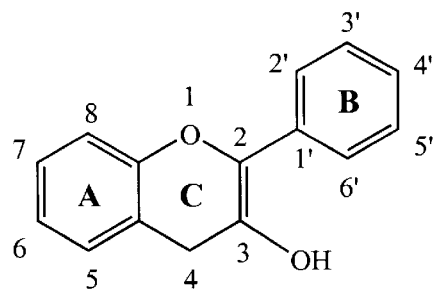
FIG. 2 is a schematic representation of the core structure of flavonols.
Figure 3:
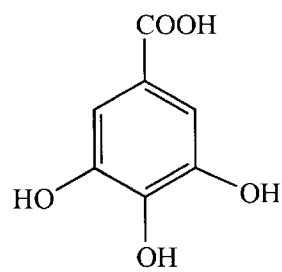
FIG. 3 is a schematic representation of the structure of gallic acid.
Figure 4:
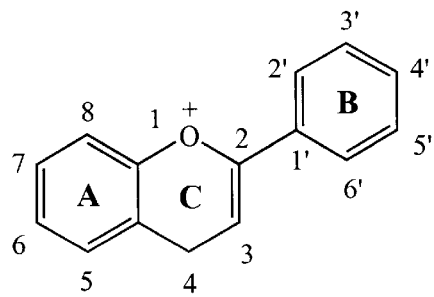
FIG. 4 is a schematic representation of the core structure of anthocyanins.
Figure 5:
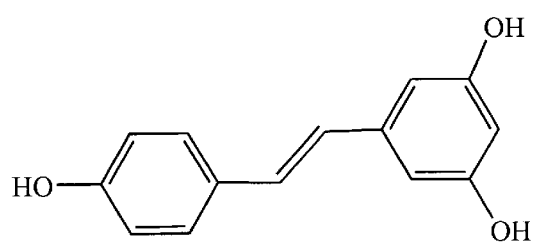
FIG. 5 is a schematic representation of the structure of resveratrol.

In a first aspect the invention discloses a method of producing a therapeutic effect in a subject by providing a dry composition suitable for human consumption, the composition including a plant-derived material with flavonol and anthocyanin, wherein at least 25% of the plant-derived material in the composition comprises polyphenols and the flavonol content is at least 0.1%.

By way of explanation plant-derived compositions may comprise extracts of plants or parts thereof (such as tubers, fruit), which may be processed in some way (e.g. by fermentation). Thus plant-derived compositions include aqueous or organic solvent extracts of plants or parts thereof, fruit juices (particularly grape juice) and fermented liquors (e.g. wine) produced from plants or fruit juice, or compositions obtained from any of the foregoing. The plant material is typically processed (physically and/or chemically) during production of the composition to extract polyphenols from the plant and so increase and enrich the polyphenol content of the composition.

Advantageously the composition may be such that the plant-derived material comprises at least 35% polyphenols, or more preferably at least 45% polyphenols.

The composition may be comprised wholly or substantially of the plant-derived material from which the flavonol content of the composition is obtained. Alternatively, the composition may comprise other material, such as flavourings, excipients, carriers and the like conventionally used in formulating compositions for human consumption.

The "plant-derived material" in the composition refers to that portion of the composition which derives from the same source as the flavonol content of the composition. The composition may also comprise other ingredients (e.g. starch or flavours) obtained from plants, but these are not to be considered as "plant-derived material" if they are not obtained from the same source as the flavonol content of the composition. Preferably, the anthocyanin content of the composition will be plant-derived material.

Preferably the composition is such that the flavonol content is at least 0.1% w/w, preferably 0.5% (w/w), more preferably at least 1% and most preferably at least 2% of the total plant-derived polyphenol content of the composition.

It is also preferred that flavonol content of the composition as a whole is at least 0.01% (w/w), more preferably at least 0.1%, and most preferably at least 1%.

In plant products, the flavonols exist in the free form (aglycone) or conjugated with sugars (glycoside). For the purpose of definition, the weight of flavonol is expressed as the aglycone. Polyphenols in wine and grape products are best analysed by HPLC, e.g. Price et al. (1995). The flavonols when separated on the chromatogram are calculated with quercitin as a standard for the aglycones and quercitrin (quercitin rhamnoside) as a standard for the glycosides.

The glycosides can be expressed as the aglycone by multiplying their concentration by:

$$\left(\frac{\text{FW quercitrin}}{\text{FW quercitin}} = \frac{302}{448}\right).$$

The total flavonol content is the sum of the aglycone contents in the free and conjugated forms.

In a further aspect the invention relates to the method of providing the therapeutic effect of the prevention or treatment of coronary heart disease in the subject.

In another aspect the invention relates to the method of providing the therapeutic effect of inhibiting oxidation of plasma LDL in the subject.

In still another aspect the invention can relate to the method of providing the therapeutic effect of stimulating TGF-β production in the subject.

Further, the invention can relate to a method of providing the therapeutic effect of inhibiting platelet aggregation or stimulating fibrinolysis in the subject.

The compositions useful in the methods defined above are typically solid at atmospheric pressure (760 mm Hg) throughout the temperature range 10–20° C. The composition may be particulate (e.g. powdered or granulated), or may be formed into capsules, tablets and the like.

The inventors have surprisingly found that compositions in accordance with the invention are effective, following oral consumption by human subjects, in inhibiting oxidation of plasma LDL, as measured by a number of criteria. Thus, the oral consumption of the composition is effective in increasing the lag phase in oxidation of isolated plasma LDL as determined by the method of Esterbauer et al (1989 Free Radic. Res. Commun. 6, 67–75). Briefly, in this method, LDL isolated from a subject's plasma by ultracentrifuge is dialysed to remove EDTA, and copper ions (5 μM) added to the LDL (present at 50 mg/L). The usual lag time before diene formation is about 50–60 min. Administration of the composition of the invention to the subject should give a prolongation of the lag time of preferably at least 2 minutes (or about 4% or more). The most preferred is in the range 5–25 minutes (or about 10–15 50%). In addition the composition is effective (following oral consumption) in reducing the amount of lipid peroxides in the plasma of human subjects (as assessed by the method of Gorog et al, 1994, and described below).

The compositions used in the methods of the present invention conveniently comprise polyphenols (including flavonols) obtained from grapes (whole grapes or parts thereof, such as skins or juice), wine (especially red wine, which comprises much higher concentrations of polyphenols than white wine), or by-products and/or waste products of the wine-making process, such as pomace (i.e. the residue of crushed grapes following juice extraction) or marc (waste solids remaining after initial fermentation). Red grape juice, especially from the Concord grape variety, is particularly rich in polyphenols and can contain up to 2.5 g/L total polyphenols and 45 mg/L flavonol. This high content of flavonol in the Concord grape is due to the variety of grape and the sunny conditions in which it is grown, since sunlight promotes the formation of flavonol in the grape skin. However, polyphenols such as flavonols are present in a wide range of naturally occurring materials, many of which contain a higher flavonol content than red wine, and so might present more appropriate sources of flavonol. Examples of such materials include: fruit in general, such as apples (e.g. var. "Gravensteiner"), especially apple peel; pears (e.g. var. "Williams Christs"); bell peppers (e.g. var. "Yolo wonder"); red currants; black currants (particularly preferred as being relatively high in flavonols); lemons; cherries; cranberries; gooseberries; tomatoes; olives; and vegetables in general, including: radishes (e.g. var. "Saxa treib"); kohlrabi (e.g. var. "Primavera"); horseradish; potatoes; onions; and asparagus.

In a particular embodiment, the composition is derived from a red wine and comprises a representative profile of substantially all the polyphenol compounds present in the wine (typically, although not necessarily, present in the composition substantially in the relative amounts representative of those in the wine from which the composition is derived). Such a composition may be referred to as a "total polyphenol pool". Another particularly good source of polyphenol compounds is grape juice.

Polyphenols may conveniently be obtained from red wine, grape juice, or other polyphenol-containing liquids by absorption onto a chromatographic resin column, with elution of the polyphenol-enriched fraction from the column (typically following a washing step) by use of a 40–80% ethanol eluent, or other suitable organic solvent (such as methanol, acetone, ethyl acetate, dimethylene chloride, and chloroform—which may be in aqueous solution). The organic solvent is preferably relatively volatile (i.e. having a boiling point of between 30 and 85° C. at 760 mm Hg pressure) and so readily driven off, to leave a substantially dry (i.e. less than 10% w/w $H_2O$) solid composition comprising polyphenols. Such a method may successfully be used to obtain a total polyphenol pool from red wine.

Alternatively, polyphenols may be obtained from red wine, grape juice, or other polyphenol-containing liquid by solvent extraction using a suitable organic solvent immiscible with the wine or other liquid. Alternatively, polyphenols may be obtained from polyphenol-containing solids by solvent extraction (typically extraction with an organic solvent such as ethanol or ethyl acetate)—the solids can then be separated from the solvent by filtration or centrifugation. The solvent may then be evaporated to leave a substantially dry, solid composition comprising polyphenols.

In preferred embodiments, the composition is presented as a food supplement. This may be a substance to add as an additional ingredient during manufacture of the foodstuff, or may be a separate substance to be consumed by an individual (e.g. as a tablet or capsule) substantially in isolation from (i.e. not mixed with) other food components prior to consumption (although, of course, the tablet or capsule may be taken with food). The invention thus includes within its scope a product, particularly a foodstuff, comprising a composition in accordance with the invention. Alternatively, the composition may be presented as a solid to be made into a drink by mixing with a physiologically acceptable diluent (such as milk, water, fruit juice, yogurt, an aqueous solution of Aloe Vera or other aqueous liquid).

The dosage of composition given to a subject is dependent on the degree of activity of the material but will be between 10 mg and 10 g per day. For the total polyphenolic pool obtained from red wine the preferred dose is 0.1–4.0 g/day, and more preferably 1–2 g/day, equivalent to 0.5 to 1 litre of red wine per day. Similar dosage levels can be used in the method of the present invention for compositions where the polyphenols are obtained from grape juice. The preferred dose of flavonol will be in the range 0.1–1000 mg per day, preferably in the range 0.5–500 mg per day, more preferably in the range 1–250 mg per day.

Those skilled in the art will be able to take the preparation of polyphenols obtained from wine, grapes, grape juice, or wine by-products and fractionate that preparation further to obtain compositions with more concentrated activity. This could be effected by column chromatography, solvent extraction, molecular sieves with semi-permeable membranes, or other method(s) conventionally used in the food industry. The advantage is that the weight of active substance is less, and the colour and taste of the supplement is modified beneficially.

Compositions in accordance with the invention may be prepared using the active polyphenol agents and anthocyanin in accordance with conventional food supplement or pharmaceutical practice. The diluents, excipients or carriers etc. which may be used are well known in the formulation art and the form chosen for any particular regimen will depend on the given context and the formulator's choice. In general the dose will depend on the concentration of polyphenols in the composition, and the identity of the polyphenol compounds in question.

Moreover, the compositions may comprise any number of further components, such as those typically used in the food industry and/or in the pharmaceutical industry. Such components may include nutrients (especially trace elements and vitamins), antioxidants, therapeutic substances (especially those having a therapeutic effect in relation to prevention and/or treatment of CHD, in particular, aspirin), flavourings, and sweeteners (especially artificial sweeteners, such as aspartame etc.).

Examples of the above include the following: a carotenoid such as lutein, lycopene, or α- and/or β-carotene; antioxidant nutrients or anti-inflammatory agents such as vitamin A, vitamin C, vitamin E (α-tocopherol and other active tocopherols), folic acid, selenium, copper, zinc, manganese, ubiquinone (coenzyme Q10), salicylic acid, 2,3-dihydroxy benzoic acid, and 2,5-dihydroxy benzoic acid.

Antioxidants such as carotenoids and vitamin E are partially destroyed in the gastro-intestinal tract by oxidation. By inclusion of these compounds in the composition of the invention it is believed that this process is inhibited and more antioxidants are absorbed. Use of a composition comprising (α-tocopherol and/or aspirin is especially preferred since it is believed that such a mixture affords a synergistic effect in the presence of polyphenols.

Typical suitable daily doses of these additional components of the composition (and which may therefore be included in the composition such that normal consumption of the composition will give the appropriate dose) are as follows:

| | |
|---|---|
| Lutein | 2 to 50 mg e.g. conveniently 7.5 mg |
| Beta carotene | 2 to 20 mg e.g. conveniently 5 mg |

-continued

| | |
|---|---|
| Vitamin A | 400 to 600 RE e.g. conveniently 500 RE |
| Vitamin C | 75 to 250 mg e.g. conveniently 100 mg |
| Folic Acid | 0.1 to 1.0 mg e.g. conveniently 0.2 mg |
| Selenium | 80 to 120 µg e.g. conveniently 90 µg |
| Copper | 2 to 4 mg e.g. conveniently 3 mg |
| Zinc | 10 to 20 mg e.g. conveniently 15 mg |
| Coenzyme Q10 | 10 to 200 mg, e.g. conveniently 30 mg |
| Aspirin | 10 to 150 mg e.g. conveniently 150 mg |

In practising the method of the present invention, the composition can take the form of capsules or tablets, each capsule or tablet containing 200 mg of polyphenol composition, with a suggested intake of one to ten capsules or tablets per day. Another presentation of the composition in the practice of the invention is as a non-alcoholic drink which provides an effective dose of polyphenols when dissolved in water (still or aerated) flavoured and sweetened to taste, or dissolved in a fruit juice e.g. grape, apple or orange etc.

Whilst it may be preferred for a number of reasons (e.g. social, religious, and economic) to provide an alcohol-free drink comprising the composition of the invention, such drinks can be fortified with alcohol (e.g. from vodka, gin, whisky) to give a desirable level of 5–50% alcohol depending on the consumer's taste.

Other presentations are as a food ingredient in dairy products such as milk and yoghurts, preserves, and dietary products intended as meal supplements or replacements. The above examples are illustrative only and are not intended to be limiting in any way.

The practice of the present invention to provide a therapeutic effect can result in inhibiting oxidation of plasma LDL in a human or animal subject; the method comprising preparing flavonol and anthocyanin-containing composition in accordance with the definition provided herein; and administering the composition to the subject; preferably by one of the above described presentations. Similarly, the method of the present invention can be carried out to result in a therapeutic effect of stimulating production of transforming growth factor (TGF)-β) in vivo. Additionally the inventors have found that oral consumption of the composition in the practice of the present invention will inhibit platelet aggregation and/or stimulate fibrinolysis, thereby decreasing the thrombotic tendency of an individual, which is of assistance in preventing and/or treating thrombotic diseases such as CHD, stroke. In particular, consumption of the composition is found to increase the level of tPA activity in plasma (as conveniently measured by means of assays such as the "Chromolize" assay [available from Biopool, Sweden] described below), the effect of which is to increase the net rate of fibrinolysis in the subject.

Thus, the practice of the method of the present invention can have a therapeutic effect in the subject in at least one or more of the following: preventing or treating coronary heart disease; inhibition of oxidation of plasma LDL; inhibition of platelet aggregation; stimulation of fibrinolysis; and stimulation of TGF-β production; the method comprising preparing a composition as described herein; if necessary or desired, mixing the composition with a physiologically acceptable excipient or carrier; and preparing unitary doses of the composition for administration to the subject. Suitable methods of making the medicaments are well-known to those skilled in the relevant art.

Medicaments having this effect may take the form of food supplements or ingredients, as explained above, and should be useful in the prevention or treatment of coronary heart disease. Suitable doses of the medicaments, as explained previously, will depend on the concentration and identity of the polyphenols in the composition, and on the severity of the disease state in the subject to be treated. However, as a general guide the dosage should preferably be sufficient to give the same amount of polyphenol consumption as that provided by the consumption of at least one glass of wine per day (approximately equivalent to 0.20 gms of the total polyphenol pool from red wine), but more preferably about 0.5–1.0 L of red wine per day (i.e. about 1.0–2.0 gms total wine polyphenol).

The invention is further described by way of the following non-limiting illustrative examples:

EXAMPLE 1

Preparation of Polyphenol Powder From Red Wine

About 2,000 litres of red wine (French 1993 Cabernet Sauvignon) was filtered to remove sediment and distilled under vacuum at 300 millibars pressure at 75 to 80° C. for 1 minute, then cooled and concentrated under vacuum at 55° C. and then quickly cooled down to 25° C. by refrigeration. The concentrated wine was passed through a column (55 cm diameter, approximately 2 metres high) containing 65 litres of Diaion HP-20 resin. The column was washed with 250 litres of distilled water and the polyphenols eluted about 250 litres of 50% ethanol, over a period of 150 minutes or so. At the end of this time the eluate was free of polyphenols, as determined by the Folin-Ciocalteu method (described by Singleton & Rossi, 1965). The eluate was then concentrated to 35% dry matter under vacuum distillation and spray dried under nitrogen to produce about 2 kg of powder with a moisture content of 3 to 4%.

The polyphenol powder is an excellent food ingredient having a dark red colour when dissolved in water or aqueous alcohol, being quite palatable, and giving a "bite" to the palate similar to that of red wine. The recommended daily dose is 1–2 g/day.

Typical composition of the polyphenol powder is compared below with the polyphenol content of red wine. Compared with red wine the polyphenol powder contains proportionally more of the proanthocyanins than the other polyphenols, but essentially preserves the relative abundance of the various polyphenols.

Composition of red wine and polyphenol powder

|  | Red wine gallic acid equiv mg/L | % | Red wine polyphenol powder mg/g | % |
| --- | --- | --- | --- | --- |
| Hydroxycinnamic acid | 165 | 15 | 18 | 3 |
| Catechins | 200 | 17 | 38 | 6 |
| Flavonols | 20 | 2 | 14 | 2 |
| Anthocyanins | 200 | 17 | 70 | 11 |
| Proanthocyanidins | 550 | 49 | 480 | 77 |
| TOTAL | 1135 |  | 620 |  |

Example 2

Preparation of Polyphenol Composition From Red Grape Juice

A sample of commercially prepared red grape juice (Welch's Concorde Grape Juice™, Orpington, UK) was used for the trial. The sample contained 2.5 g/L polyphenols and had a dry weight of 177 g/L.

A comparison of two resins, Diaion™ HP-20 and Sepabead™ SP70 (Mitsubishi, New York) was made. For the HP-20 resin the treatment was similar to that in Example 1, except that the grape juice was not dealchoholised. Grape juice (250 ml) was added to 50 g HP20 or SP70 absorbent. The column was washed with water (4 bv) to remove sugars and the polyphenols eluted with 125 ml 75% aqueous ethanol. The eluent was made up to the original volume of the grape juice (250 ml) with water. For the HP-20 absorbent, the polyphenol content of the eluent was 1.65 g/L. the dry weight of the diluted eluent was 2.27 g/L and the solid had a polyphenol content of 72.6%.

Exactly the same procedure was conducted using the SP70 absorbent. In this case the polyphenol content of the eluent was 1.53 g/L, the dry weight of the eluent was 2.09 g/L and the polyphenol content of the dry solid was 73.1%.

Table 1 shows the results of analyzing a sample of the red grape juice, and the eluents from the HP-20 and SP70 absorbents. Since the eluents were made up with water to the original volume of the grape juice jused, the analyses can be directly compared. The grape jice has a high concentration of flavoonols amounting to 41.7 mg aglycone/L most of which were glycosides. As expected the concentration of the aglycone was low, being only 0.7 mg/L, because the aglycone is only found in high concentration in fermented grape juice, for example red wine.

Using 75% aqueous ethanol as the eluting solvent, the yield of flavonol was very high and the concentration of flavonol in the eluent virtually identical to the original grape juice (allowing for experimental error). There was no apparent difference between the HP-20 and SP70 absorbents in their efficacy to remove flavonols. For the HP-20 absorbent the calculated flavonol content of the dry powder was 25.1 mg aglycone/g polyphenol (2.51%) and for the SP70 absorbent it was 28.1 mg aglycone/g polyphenols (2.81%).

TABLE 1

Polyphenol concentrations in red grape juice and eluent from HP20 and SP70 absorbents

| Polyphenol* | Red Grape Juice Mg/L | Eluent from HP20 mg/L | Eluent from SP70 mg/L |
| --- | --- | --- | --- |
| 1 gallic acid | 7.1 | 0.4 | 1.7 |
| 2 procyanin dimers | 10.6 | 13.7 | 11.3 |
| 3 catechin | 15.7 | 12.1 | 16.1 |
| 4 epicatechin | 7.5 | 6.7 | 6.6 |
| 5 polymeric paenols | 277 | 252 | 221 |
| 6 caftaric acid | 49.3 | 25.8 | 36.6 |
| 7 caffeic acid | 3.6 | 3.2 | 3.6 |
| 8 coutaric acid | 12.6 | 9.9 | 12.3 |
| 9 O-coumaric acid | 2.1 | 1.9 | 1.7 |
| 10 trans resveratrol | <0.1 | <0.1 | <0.1 |
| 11 cis resveratrol | <0.1 | <0.1 | <0.1 |
| 12 myricetin glycosides | 28.4 | 27.9 | 29.8 |
| 13 quercetin glycosides | 33.0 | 34.0 | 33.5 |
| 14 myricetin | 0.3 | 0.4 | 0.4 |
| 15 quercetin | 0.3 | 0.3 | 0.2 |
| 16 delphinidin glycoside | 1.0 | 1.6 | 1.2 |
| 17 peonidin glycoside | 2.9 | 3.9 | 4.7 |
| 18 petunidin glycoside | 1.3 | 1.5 | 1.0 |
| 19 malvidin glycoside | 3.1 | 2.7 | 2.2 |
| 20 polymeric anthocyanins | 13.2 | 12.4 | 10.7 |
| 21 delphinidin diglucoside | 1.7 | 1.1 | 1.0 |
| 22 cyanidin diglucoside | 4.3 | 5.6 | 5.9 |
| 23 peonidin diglucoside | 9.8 | 11.7 | 11.3 |
| 24 petunidin diglucoside | 1.7 | 2.5 | 2.4 |
| 25 malvidin diglucoside | 4.5 | 5.0 | 3.7 |

*Peak 1 was quantified as gallic acid, peaks 2, 3, 4, 5, 27 and 27 as catechin, peaks 6 through 9 as caffeic acid, peaks 10 and 11 as trans resveratrol, peaks 12 and 13 as quercetrin, peaks 14 and 15 as quercetin, peaks 16 through 25 as malvin.
+made up to same volume as original grape juice with water

EXAMPLE 3

Volunteer studies using wine polyphenols were conducted in order to determine the antioxidant activity of red and white wine and polyphenol preparations in healthy volunteers.

Subjects and Methods 26 healthy men, aged 35 to 65, who were non-smokers, consuming a standard UK diet participated in a private and confidential study. Two weeks before the study the volunteers discontinued wine consumption. All the volunteers were asked to maintain their usual diet and lifestyle during the study. The volunteers were divided into groups which consumed the following wine or tea products with meals for two weeks in the quantities shown in Table 2. The red wine was Cabernet Sauvignon (1993) and the white wine was from the region of Narbonne, France. The wine provided during the study was the only wine allowed during the experimental period. In addition the same subjects were given polyphenol powder prepared from the same batch of red wine used in the study. The powder was stored at $-20°$ C. (PP1) and a fresh sample prepared in June 1996 (PP2). The studies commenced at the beginning of September 1995 and lasted about one year.

Group Test Substance
1) Cabernet Sauvignon red wine (375 ml), containing 1.8 gms/L polyphenols
2) Vin ordinaire white wine (375 mls), containing 0.2 gms/L polyphenols
3) red wine pp powder (prepared from the same wine as given to group 1), 1 gm in two gelatine capsules
4) white wine containing in solution 1 gm red wine polyphenols (see below)
5) vodka and lemonade (10% v/v alcohol), 400 mls per day
6) 50 mgs/day anthocyanins, as grape skin extract (Sefcal, St Julien de Peyrolas, France) given as a drink
7) red wine marc (French Paradox™, Arkopharma, Nice, France) given as capsules (3 per day), each capsule comprising 250 mg marc
8) grape seed proanthocyanidins, as Endotelon™ capsules, (Sanofi-Winthrop, France) (3 per day), each capsule comprising 150 mg proanthocyanidin
9) green tea extract (Polyphenon™, Mitsui Norin, Fujieda, Japan), 3 capsules per day, each capsule comprising 100 mg tea catechins as follows: 1.6% gallo catechin, 19.3% epigallo catechin, 6.4% epi catechins, 59.1% epigallo catechin gallate and 13.7% epicatechin gallate Blood samples were drawn into $K_3$ EDTA (1 mmol/L) 12 hours after the supper meal, before and at the end of the period of wine product consumption. Samples were centrifuged at 2000×g for 15 minutes at 4° C. to obtain plasma. LDL was separated by density gradient ultracentrifugation using a Beckman bench top model Optima TLX with a TLA 100.4 rotor (Beckman, Palo Alto, Calif.), as follows: sodium bromide was added to plasma to a density of 1.3 g/ml and layered under a 1.006 g/ml density solution. Spinning took place at 100,000 RPM for 20 minutes at 4° C. The orange/yellow LDL band was removed and spun with 1.154 and 1.063 g/ml density solutions for 30 minutes at 100,000 RPM and 4° C.

The visible LDL layer was removed and dialysed with 10 mM phosphate buffered saline with 2 $\mu$M EDTA for one hour using a dialysis cassette (Pierce Slide-A-Lyzer, Perstorp Biotec Company, USA) at 4° C. for one hour, then with 10 mM phosphate buffered saline overnight.

Total polyphenols were determined in plasma and in the LDL fraction by the method of Singleton and Rossi (1965). Briefly, total polyphenols in plasma and LDL were measured by taking 125 $\mu$l of plasma or 400 $\mu$l of LDL and making up to 500 $\mu$l with water. This mixture was added to 2.5 mls of Folin reagent (diluted 1:10) and 2.0 $\mu$ml of sodium carbonate (75 gm/L). After mixing well the solution was incubated at room temperature for 2.5 hours and then centrifuged at 2,500 rpm for 8 minutes. The optical density of the supernatant was measured at 765 nm. Gallic acid was used as a standard for comparison.

Protein was determined by the Bradford Method (Bradford, 1976) using a kit containing the Bioquant reagent (Merck, Darmstadt, Germany).

Two independent methods were used to determine antioxidant activity.

1) Copper oxidation of LDL

Figure 6:
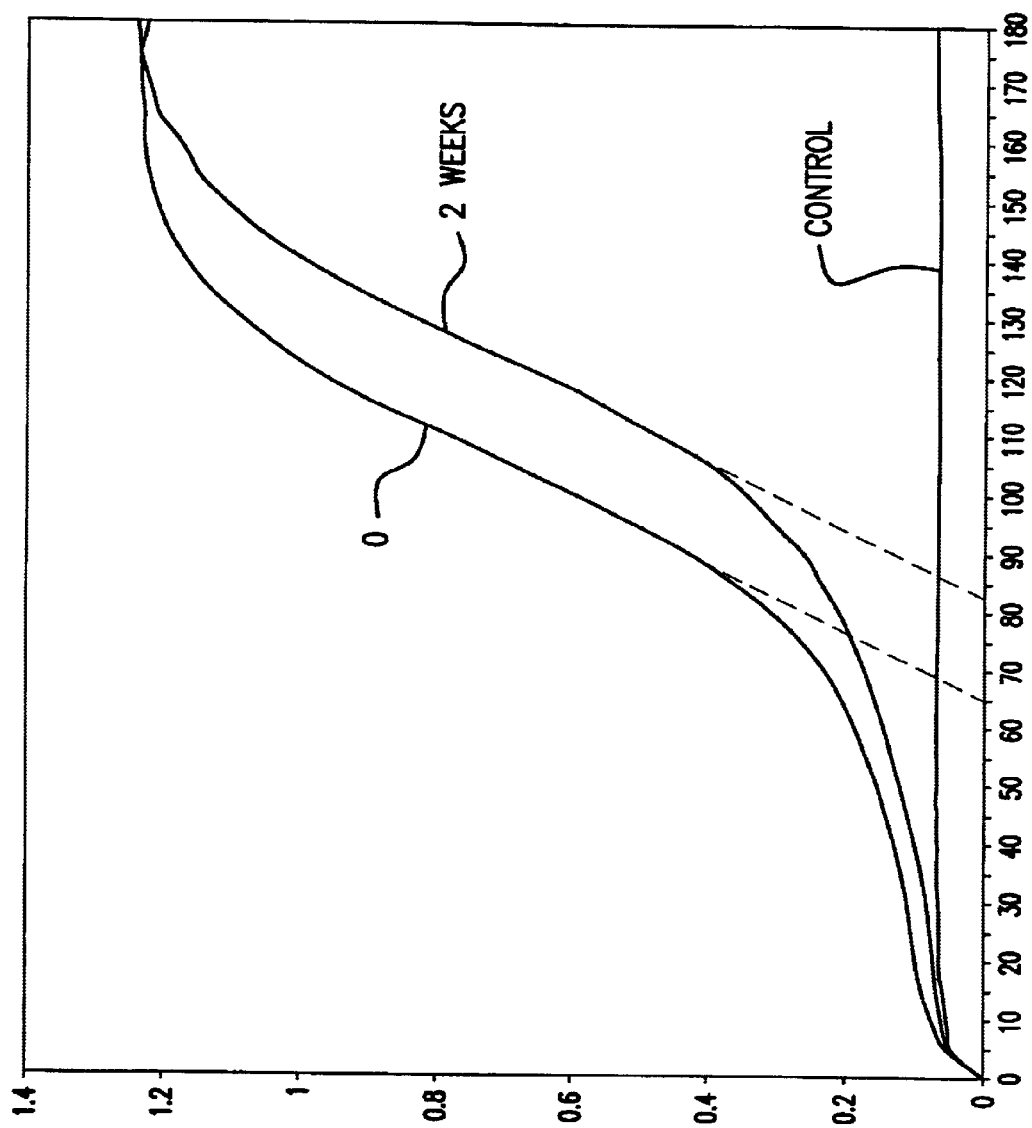
FIG. 6 shows a graph of LDL oxidation against time (minutes).

The lipoprotein (50 mg LDL protein/L) was incubated in the presence of copper sulphate (5 mM) at 37° C. for 5 hours. Conjugated diene formation was continuously monitored by measuring the increase in absorbance at 234 nm and the lag time before diene-formation determined according to the method of Esterbauer, et al. (1989). FIG. 6 shows a graph of conjugated diene formation (as measured by absorbance at 234 nm) against time (in minutes). Typical curves are illustrated for samples taken at the start of the trial (0) and after 2 weeks. The lag phase is measured by extrapolating the linear part of the plots down to the x axis (as shown by the broken lines). Preferably, consumption of compositions in accordance with the invention will result in an increase of lag phase time of 2 minutes or more.

2) Plasma Lipid Peroxides

All plasma lipids and lipoproteins were selectively removed using PHM-L-liposorb (Calbiochem-Novabiochem UK). Dry PHM-L-liposorb (20 mg) was suspended in 0.25 ml of 150 mM sodium chloride containing 10 mM sodium citrate in a 2 ml brown micro centrifuge tube, the contents stirred and allowed to equilibrate for 5 minutes. Plasma (0.5 ml) or saline (blank) was then added to the liposorb suspensions, stirred and the tubes placed on a rotating mixer for 15 minutes. After centrifugation (12,000×g for 1 min) the supernatant was discarded and liposorb gel washed twice by 1.5 ml saline followed by stirring and centrifugation. The washed liposorb gel was suspended in 1.5 ml cholesterol oxidase-iodide reagent (BDH-Merck) and placed on a rotating mixer and stirred for 60 mins. After centrifugation (12,000×g for 3 min) at room temperature the optical density of the clear supernatant was measured in a spectrophotometer at 405 nm against a blank with saline, (Gorog et al, 1994).

Preferably consumption of compositions in accordance with the invention will result in a decrease in plasma lipid peroxide concentration of at least 0.1 $\mu$mol/g protein.

Results

The values obtained were compared before and after treatment. Table 2 summarises the results which are given in detail in Tables 3 to 7. As shown in Table 2, those products containing abundant wine polyphenols (red wine, PP1, PP2, white wine+PP1) showed an increase in polyphenols in plasma and LDL and antioxidant activity in LDL, as measured by tests 1 and 2 above.

The two polyphenol powders (PP1, PP2) gave results of the same magnitude as the equivalent amount of red wine.

There was no effect with white wine, anthocyanin powder (Sefcal™, an extract from grape skins used as a food colorant) red wine pomace, French Paradox™ capsules (Arkopharma) or Endotelon™ (Sanofi-Winthrop, a proanthocyanidin preparation from grape seeds), nor with the green tea extract (Polyphenon™) containing catechins and their esters.

The active polyphenol preparation contained the pool of all the polyphenols in the red wine, and was carefully processed so as to avoid their oxidation. Moreover it was shown that the polyphenol content of the plasma and isolated LDL was raised in those subjects receiving red wine or polyphenol powder obtained from red wine or grape skins.

In confirmation of the antioxidant activity of the preparation, a second assay was used in which plasma was treated with an absorbent resin which removed lipids and lipoproteins and the content of lipid peroxides determined in the resin. The content of lipid peroxides were decreased in the subjects given red wine or the polyphenol preparation. Again the magnitude of the effect of the polyphenol powder was equivalent to the amount of red wine from which it was obtained.

These experiments show conclusively that polyphenols are absorbed after red wine ingestion and appear in the plasma and LDL, and that polyphenols isolated from wine can have a similar effect. Moreover the absorbed polyphenols have powerful antioxidant activity. The mode of action of the polyphenols may be several. Primarily they can sequester metal ions such as copper and iron which promote the production of lipid peroxides in vivo. These chelated ions are inactive as pro-oxidants. Polyphenols, because of the high content of hydroxy groups, comprise chemical structures known to chelate metal ions, and thus destroy their catalytic properties.

Another action may be to act as a sacrificial substance which is oxidised before LDL, as is the case for alpha-tocopherol. However the invention is not limited to any one particular mode of action.

To investigate the importance of the removal of EDTA from the preparation before copper catalyst oxidation, a comparison was made using dialysis with and without EDTA, and a resin column method. When EDTA is added to the dialysate the prolongation of the lag time produced by red wine polyphenol powder did not occur or was markedly reduced. Dialysis without EDTA and the column method gave similar results. The failure of previous authors (de Rijke et al, 1996) to obtain an effect of red wine in volunteers might be explained by the presence of EDTA in their preparations used for copper catalysed oxidation.

TABLE 2

Summary of results of volunteer studies on wine polyphenols

| Product | No. | Polyphenols Plasma | LDL | Antioxidant LDL Copper method | Activity Plasma Lipid Peroxides |
|---|---|---|---|---|---|
| Red wine | 9 | + | + | + | + |
| White wine | 9 | − | − | − | − |
| PP1 powder | 9 | + | + | + | + |
| PP2 powder | 6 | + | + | + | + |
| White wine + PP1 | 6 | + | + | + | + |
| Alcoholic drink | 6 | − | − | − | − |
| Anthocyanins | 5 | − | − | − | − |
| Red wine Marc | 6 | − | − | − | ND |
| Grape seed proanthocyanidins | 6 | − | − | − | − |
| Green tea extract | 7 | − | − | − | ND |

+ = positive effect
− = no effect
ND = not done

TABLE 3

Effect of wine and wine products on plasma polyphenols mg/gm protein ± (S.D.)

| Product | No | 0 | 2wk | P value paired t test |
|---|---|---|---|---|
| Red wine | 9 | 16.2 ± 5.6 | 22.6 ± 2.7 | 0.008 |
| White wine | 9 | 18.9 ± 5.0 | 20.3 ± 1.4 | 0.450 |
| PP1 | 9 | 21.0 ± 2.9 | 26.9 ± 5.3 | 0.009 |
| PP2 | 6 | 24.5 ± 1.4 | 26.0 ± 1.8 | 0.070 |
| White wine + PP1 | 6 | 17.6 ± 4.0 | 22.6 ± 1.7 | 0.020 |
| Alcoholic drink | 6 | 23.9 ± 1.0 | 24.0 ± 1.2 | 0.860 |
| Anthocyanins | 5 | 19.2 ± 6.4 | 21.4 ± 3.1 | 0.580 |
| Red wine Marc | 6 | 22.6 ± 0.7 | 23.4 ± 1.2 | 0.158 |
| Grape seed proanthocyanidins | 6 | 20.4 ± 6.7 | 21.3 ± 7 | 0.380 |
| Green tea extract | 7 | 21.3 ± 1.2 | 22.1 ± 1.6 | 0.295 |

TABLE 4

Effect of wine and wine products on LDL polyphenols (mg/gm protein ± S.D.)

| Product | No | 0 | 2wk | P value paired t test |
|---|---|---|---|---|
| Red wine | 9 | 34.0 ± 6.2 | 42.3 ± 8.1 | 0.001 |
| White wine | 9 | 39.3 ± 6.1 | 38.5 ± 10.0 | 0.820 |
| PP1 | 9 | 37.0 ± 4.6 | 47.6 ± 6.2 | 0.002 |
| PP2 | 6 | 35.5 ± 5.1 | 46.0 ± 10.0 | 0.006 |
| White wine + PP1 | 6 | 33.5 ± 6.3 | 54.2 ± 21.0 | 0.040 |
| Alcoholic drink | 6 | 39.4 ± 4.5 | 43.7 ± 1.6 | 0.084 |
| Anthocyanins | 5 | 40.0 ± 5.6 | 36.2 ± 6.0 | 0.520 |
| Red wine Marc | 6 | 41.7 ± 3.6 | 38.4 ± 3.4 | 0.063 |
| Grape seed proanthocyanidins | 6 | 38.2 ± 4.8 | 40.2 ± 3.7 | 0.240 |
| Green tea extract | 7 | 36.9 ± 6.2 | 37.3 ± 5.3 | 0.840 |

TABLE 5

Effect of wine and wine products on plasma lipid peroxides ($\mu$mole/g protein (±S.D.)

| Product | No | 0 | 2wk | P value paired t test |
|---|---|---|---|---|
| Red wine | 9 | 2.13 ± 0.70 | 1.54 ± 0.48 | 0.056 |
| White wine | 9 | 1.73 ± 0.55 | 2.15 ± 0.66 | 0.158 |
| PP1 | 9 | 1.90 ± 0.52 | 1.37 ± 0.38 | 0.051 |
| PP2 | 6 | 1.88 ± 0.24 | 1.51 ± 0.21 | 0.018 |
| White wine + PP1 | 6 | 1.70 ± 0.51 | 1.19 ± 0.19 | 0.040 |
| Alcoholic drink | 6 | 1.60 ± 0.25 | 1.50 ± 0.40 | 0.460 |

TABLE 5-continued

Effect of wine and wine products on plasma lipid peroxides
(μmole/g protein (±S.D.))

| Product | No | O | 2wk | P value paired t test |
|---|---|---|---|---|
| Anthocyanins | 5 | 3.04 ± 0.73 | 2.93 ± 0.56 | 0.260 |
| Red wine Marc | 6 | | not done | |
| Grape seed proanthocyanidins | 6 | 1.69 ± 0.13 | 1.47 ± 0.46 | 0.289 |
| Green tea extract | 7 | | not done | |

TABLE 6

Effect of wine and wine products on LDL oxidation by copper: mean
lag time in minutes (±S.D.)

| Product | No | O | 2wk | P value paired t test |
|---|---|---|---|---|
| Red wine | 9 | 51.6 ± 7.6 | 69.3 ± 18.3 | 0.008 |
| White wine | 9 | 63.8 ± 18.5 | 63.6 ± 9.9 | 0.950 |
| PP1 | 9 | 51.7 ± 5.6 | 65.9 ± 12.8 | 0.006 |
| PP2 | 6 | 60.0 ± 9.2 | 73.7 ± 11.0 | 0.001 |
| White wine + PP1 | 6 | 54.8 ± 2.6 | 66.5 ± 5.2 | 0.007 |
| Alcoholic drink | 6 | 54.0 ± 4.6 | 56.6 ± 4.2 | 0.140 |
| Anthocyanins | 5 | 53.0 ± 4.4 | 51.5 ± 3.11 | 0.650 |
| Red wine Marc | 6 | 62.0 ± 2.7 | 60.3 ± 5.2 | 0.500 |
| Grape seed proanthocyanidins | 6 | 69.5 ± 24.0 | 62.8 ± 5.4 | 0.499 |
| Green tea extract | 7 | 66.2 ± 4.4 | 59.3 ± 5.4 | 0.629 |

Conclusions

The antioxidant activity of 1 gram wine polyphenol powder is equivalent to half a bottle of red wine. A daily dose of 1–2 g polyphenol powder would have potential prophylactic activity against coronary heart disease. Other products such as grape skin extract used in the food industry as a colorant, a proanthocyanidin preparation, French Paradox capsules and a green tea extract containing catechins and their esters were inactive.

EXAMPLE 4

A capsule was prepared from the following ingredients by simple admixture and routine encapsulation.

| | mg |
|---|---|
| Wine polyphenol powder | 500 |
| Stearic acid | 25 |
| Magnesium stearate | 50 |
| Microcrystalline cellulose | 25 |
| | 600 mg |

Two to four capsules are taken daily with or after meals.

EXAMPLE 5

A capsule was prepared from the following ingredients by simple admixture and routine encapsulation.

| | mg |
|---|---|
| Wine polyphenol powder | 400 |
| α tocopherol | 150 |
| Folic acid 0.2 mg (1:50 in diluent) | 10 |
| Lecithin | 20 |
| Beeswax | 20 |
| | 600 mg |

At least three capsules per day should be taken with meals.

EXAMPLE 6

One gram wine polyphenolic powder is added to dry powder formula diet composition providing 405 Kcal per day (42 g protein, 43 g carbohydrate and 8 g fat, RDA of vitamins and minerals) retailed under the trade name Cambridge Diet (Cambridge Health Plan Ltd, Norwich, UK). One day's supply (3 meals/day) provides an intake of polyphenols equivalent to 0.5 L red wine/day.

EXAMPLE 7

0.5 g of total polyphenol pool obtained from red wine is added to 250 ml plain yoghurt containing strawberry flavour and sweetener. The red coloured polyphenol material enhances the appearance of the yoghurt, and provides a highly palatable food stuff with health benefits.

EXAMPLE 8

The following formulation is that of a non-alcoholic drink provided as a powder to be mixed with water.

| | |
|---|---|
| Dextrose monohydrate | 300 g |
| Citric Acid | 32 g |
| Tri sodium citrate | 5 g |
| Grapefruit flavour | 6 g |
| Lemon flavour | 1.4 g |
| Orange flavour | 1.4 g |
| Aspartame | 1 g |
| Total wine polyphenol pool (as example 1) | 21 g. |

53 g of the powder is dissolved in 1 litre of water. A serving of 250 ml provides 0.75 g of active polyphenols.

The beneficial properties of the drink can be improved by the substitution of 100 ml water for 100 ml Aloe Vera gel. It is within the concept of the invention to provide an embodiment of the invention as the red wine extract with Aloe Vera.

EXAMPLE 9

The following is an alcoholic drink provided as a bottled ready-to-drink mix.

| | |
|---|---|
| Deaerated tonic water | 450 ml |
| Vodka | 50 ml |
| Total wine polyphenols (as example 1) | 1 g |

The polyphenol is dissolved in the flat (deaerated) tonic mix and then gassed with carbon dioxide under pressure to give an aerated drink. Aliquots of 450 ml are dispensed into bottles, the Vodka added and the bottle sealed with a screw cap.

EXAMPLE 10

About 2000 Kg pomace obtained from white grapes was well stirred in a commercial mixer with 2500 L distilled water at 30° C. for four hours. The mixture was then removed from the mixer and placed in a tank and allowed to settle for two hours, the supernatant was then drawn off and filtered to give a clear liquid. The same procedure was then employed as in example 1 for absorption of the polyphenols on the resin using similar quantities of Diaion HP-20 resin and eluting solvent.

On concentration of the aqueous ethanol solution to 35% dry matter a red coloured solid appeared weighing approximately 600 g. This was soluble in 10% aqueous alcohol and was then spray dried to give a solid insoluble in water but soluble in aqueous alcohol. The remaining solution was then spray dried under nitrogen to give 1.4 Kg of a red coloured material containing about 50% polyphenols. The composition of this was similar to that obtained in example 1.

This method has the disadvantage that the procedure to obtain the extract before absorption on the resin is more difficult and time consuming. Although the yield is less, the availability of grape skins cheaply has commercial advantages.

The powdered drink was reconstituted and administered to 5 volunteers for two weeks according to the protocol described in Example 3. The results in the copper catalysed LDL oxidation assay were as follows:

| Before | 78.8 ± 7.2 min |
| After 2 wk | 93.0 ± 9.4 min |
| Change | 14.2 ± 4.8 min |
| (p value 0.003) | |

It is concluded that an extract from grape skins (in this case white grapes), i.e. pomace, could be an effective antioxidant when taken orally for 2 weeks.

EXAMPLE 11

Plasma LDL (from the cohort of volunteers described in Example 3) was separated by ultracentrifugation and dialysed against phosphate buffer as described in Example 3. Polyphenol containing substances were analysed for their polyphenol content by the method of Singleton & Rossi (1965). Plasma LDL (0.05 $\mu$kg LDL in 1.0 ml) was incubated with 100$\mu$l copper sulphate solution (final concentration 5 $\mu$M) at 37° C. and the lag time determined by the copper catalysed diene assay, as described in Example 3. The ability of the polyphenol containing substances to prolong the lag time in vitro was determined by adding 4$\mu$g of polyphenol substance to 1 ml of LDL prior to the addition of the copper sulphate. The substances tested were as follows:

1) Cabernet Sauvignon red wine
2) Vin ordinaire white wine
3) Red wine polyphenols, prepared as described in example 1
4) Sefcal™ anthocyanin, as described in Example 3
5) Endotelon™ proanthocyanidins, as described in Example 3
6) French Paradox capsules (red wine marc), as described in Example 3
7) Polypheno™ (green tea catechins), as described in Example 3

The results obtained in vivo by oral consumption of the test substances for 2 weeks are compared with the in vitro results in Table 8 below. The in vitro results are a mean of four determinations. The lag time was increased with all substances added at a level of 4 $\mu$g/ml. The order of the magnitude of effect observed was: polyphenol powder=anthocyanins>green tea catechins>grape seed proanthocyanidins>red wine>white wine>red wine marc.

When the substances were taken orally and LDL separated and tested as described in Example 3, only red wine and red wine polyphenols gave a prolongation of the lag time, all the other polyphenol containing substances were inactive. This clearly shows that it is impossible to predict the in vivo effect of a substance from in vitro results. The lack of activity of most of the substances in vivo might be due to their lack of absorption from the gut, or failure to be incorporated into LDL.

TABLE 7

A comparison of polyphenol containing substances in vitro and in vivo, in the copper-diene assay.

| | | In vitro Increase in lag time | | | In vivo Increase in lag time | | | |
| --- | --- | --- | --- | --- | --- | --- | --- | --- |
| Substance | Polyphenol content | min | % | effect** | Polyphenol intake/day | min | % | Effect |
| Red wine | 1.8 g/L | 26 | 100 | ++ | 675 | 17.8 | 100 | ++ |
| White wine | 0.2 g/L | 22 | 85 | + | 75 | −0.22 | −1 | − |
| Polyphenol powder* | 450 mg/g | 65 | 230 | +++ | 450 | 14.2 | 80 | ++ |
| Red wine anthocyanins | 500 mg/g | 66 | 255 | +++ | 500 | −1.5 | −8 | − |
| Grape seed pro-anthocyanins | 425 mg/g | 50 | 190 | +++ | 750 | −6.7 | −38 | − |
| Red wine Marc | 210 mg/g | 18 | 70 | + | 156 | −1.7 | −10 | − |

TABLE 7-continued

A comparison of polyphenol containing substances in vitro and in vivo, in the copper-diene assay.

| | | In vitro Increase in lag time | | | In vivo Increase in lag time | | | |
|---|---|---|---|---|---|---|---|---|
| Substance | Polyphenol content | min | % | effect** | Polyphenol intake/day | min | % | Effect |
| Green tea catechins | 960 mg/g | 75 | 290 | +++ | 300 | −6.8 | −38 | − |

*in capsules
**Effects observed:
+ small,
++ moderate,
+++ large,
− none.

EXAMPLE 12

Twenty of the above mentioned volunteers from Example 3 were divided into groups (A and B) of 6–9 subjects and were given for two weeks:
A) A blackcurrant flavoured drink (330 ml) containing 1 g total red wine polyphenols and mixed with a commercially available powder (sugar, citric acid, sodium citrate aspartame, synthetic flavour; Cambridge Manufacturing Co Ltd, Corby, UK) to which water was added immediately prior to consumption; or
B) Capsules containing red wine polyphenol powder as prepared above in a dose of 2 g red wine polyphenols/day.

The products were divided equally and taken after lunch and dinner.

Plasma samples were obtained and spun in an ultracentrifuge to obtain LDL as described in Example 3.

Three methods of treating the LDL before oxidation were employed as below.

a) Final dialysis without EDTA. LDL was dialysed with 10 mM phosphate buffer saline containing 2 $\mu$M EDTA for one hour using a dialysis cassette (Pierce Slide-A-Lyzer Perstorp Biotec Company, USA) at 4° C. for one hour, then with 10 mM phosphate buffer saline overnight.

b) Continuous dialysis with EDTA LDL was removed and dialysed at 4° C. as above except that dialysis throughout was with 10 $\mu$M EDTA in 10 mM phosphate buffered saline.

c) Column treatment
LDL was passed through an EcNo-pac 10 DG desalting column (Bio-Rad Labs, UK). The column was washed twice with treated 10 mM PBS [chelex-100 resin (Bio-Rad, UK), 5 g/L PBS mixed and decanted]. 600 $\mu$L LDL was then loaded on the column and eluted with 3 ml PBS buffer at a flow rate of 0.6 ml/min using an Ismatec IPC Peristaltic pump (Ismatec, Weston Super Mare, UK).

Copper catalysed peroxidation was then performed and the lag time measured as in Example 3. The results are shown in Table 8.

Red wine polyphenol consumption either as a drink (1 g/day) or capsules (2 g/day) produced an increase in lag time (when EDTA was omitted from the final dialysate) of 30% and 21% respectively and also by the column method of 12% and 22% respectively. The addition of EDTA to the dialysate abolished the effect with 1 g/day red wine polyphenols and gave only a small increase in lag time of 7% with 2 g/day.

TABLE 8

Lag times (min) in copper-catalysed peroxidation using different methods for desalting LDL

| Supplement | No | Dialysis Without EDTA | Dialysis With EDTA | No Dialysis Column |
|---|---|---|---|---|
| Wine Polyphenols | | | | |
| Drink (1g/day) | 6 | | | |
| Baseline | | 60.0 ± 5.3 | 64.3 ± 3.8 | 54.2 ± 4.6 |
| After 2 weeks | | 77.7 ± 8.4 | 64.5 ± 3.9 | 60.6 ± 4.7 |
| Difference of means | | 17.7 ± 3.1 | 0.3 ± 0.1 | 6.4 ± 0.1 |
| P-value | | 0.02 | 0.9 | 0.005 |
| Capsules (2 g/day) | 6 | | | |
| Baseline | | 62.7 ± 2.5 | 67.7 ± 3.6 | 54.0 ± 2.2 |
| After 2 weeks | | 75.8 ± 2.8 | 72.2 ± 3.1 | 65.8 ± 2.2 |
| Difference of means | | 13.2 ± 0.3 | 4.5 ± 0.5 | 11.8 ± 0.1 |
| P-value | | 0.004 | 0.02 | 0.003 |

It is within the scope of the present invention to provide an active polyphenol preparation (conveniently derived from grapes, grape juice, wine or wine by-products) for the treatment of coronary heart disease and other diseases associated with smooth muscle cell proliferation such as atherosclerosis, restenosis, stroke and neoplasias of the bowel and uterus, uterine fibroid or fibroma.

The inventors have surprisingly found that it is possible to prepare a polyphenol composition (e.g. from red wine) which when given orally to a human subject will stimulate the production of total and active TGF-$\beta$-1. Similarly a therapeutic effect can be effected in a subject when the flavonol and anthocyanin containing compound used in the method of the present invention is derived from grape juice.

It has been demonstrated that when red wine or a preparation of polyphenols obtained from red wine provided as a powder or a drink are administered orally to man there is an increase in plasma total and active TGF-$\beta$-1. The level of polyphenol content in grape juice also makes it a good source of polyphenols for the composition used in the method of the present invention. White wine which contains little polyphenols is inactive.

The dosage of polyphenol preparation is dependent on the degree of activity of the material but will be between 10 mg and 10 g per day. For the total polyphenolic pool obtained from wine the preferred dose is 0.1–4 g/day and more preferably 1–2 g/day equivalent to 0.5 to 1 litre of red wine per day. The desired level of dosage for compositions wherein the plant-derived material is taken from grape juice would be similar to that of wine.

EXAMPLE 13

Red wine, white wine and a preparation of polyphenols obtained from red wine (as described previously in example 1) in the form of a powder or drink given by oral administration to human subjects, have been studied for their effects on plasma TGF-β.

Healthy volunteers (30 men aged 35 to 65 years) were asked to discontinue wine consumption for two weeks. They were given either 375 ml of red wine or white wine or 1 g total pool of red wine polyphenols (prepared from the same Cabernet Sauvignon wine as above) either as capsules or as a flavoured drink in 330 ml water. Each supplementation was consumed twice daily after meals for a period of two weeks.

Blood samples were drawn into $K_3$ EDTA (1 mmol/L) after treatment and centrifuged to obtain the plasma, which was stored at −70° C. prior to analysis. Total plasma polyphenols were measured by the method of Singleton and Rossi (1965). Total TGF-β-1 was determined by immunoassay using two different polyclonal antibodies (methods 1 & 2, described below):

Method 1

Total (latent+active) TGF-β was measured by a Quantikine® human TGF-β immuno assay kit supplied by R&D systems (Abingdon, Oxford, UK). This assay employs the quantitative sandwich immunoassay technique. TGF-β soluble receptor type II binds TGF-β-1 which has been precoated on a microtitre plate. Standards and samples are pipetted into the wells and any TGF-β-1 present is bound by the immobilized receptor. After washing away any unbound substances an enzyme linked polyclonal antibody specific for TGF-β-1 is added to the wells to sandwich the TGF-β-1 immobilized during the first incubation. Following a wash to remove unbound antibody enzyme reagent a substrate solution is added to the wells which produces a colour with the enzyme. The intensity of the colour developed is proportional to the TGF-β-1 present.

Before carrying out the assay, latent TGF-β is converted into the active form by adding acetic acid and urea, incubating for 10 minutes and then neutralising with sodium hydroxide/HEPES solution. The method estimates (latent+active) TGF-β-1. Activation of latent TGF-β was performed as follows: to 0.1 ml of plasma, 0.1 ml of 2.5N acetic acid/10M urea was added, mixed well and incubated for 10 minutes at room temperature. To this solution 0.1 ml of 2.7N NaOH/1M HEPES was added to neutralise the sample, and mixed well. Prior to assay the activated plasma sample was diluted 10-fold with calibrator diluent serum RD6M supplied by the kit manufacturer.

The assay procedure was as follows: 200 μl of sample or standard was added to each well of the microtitre plate. The plate was then covered with an adhesive strip of plastics material and incubated for 3 hours at room temperature. Each well was then aspirated and washed three times with 400 μl of washing buffer. 200 μl of TGF-β1 conjugate was then added to each well and the plate again covered with a fresh adhesive strip and incubated at room temperature for 110 minutes. Wells were then aspirated and washed three times with 400 μl of washing buffer. 200 μl of substrate solution was added to the wells and the plate incubated for 20 minutes at room temperature. 50 μl of 2N $H_2SO_4$ solution was then added to each well and the optical density measured at 450 nm.

Method 2

Essentially the same method was employed as above except that TGF-β was not activated before estimation and instead of the polyclonal antibody for TGF-β-1 a BDA-19 antibody (R&D systems, Abingdon, Oxford, UK) was used instead. This method estimates an active form of TGF-β-1.

Preferably, consumption of a composition in accordance with the invention will produce an increase of TGF-β1 levels in the subject by at least 1.5 ng/ml as judged by Method 1, or at least 0.5 ng/ml as judged by Method 2.

Results

As shown in Table 9, plasma polyphenols were increased in red wine but not with white wine, and with the polyphenol capsules and drink. An increase in TGF-β-1 was observed by both methods in red wine, and with the polyphenol capsules and drink but not white wine. This indicates that red wine polyphenols increase both the total amount (latent+active) TGF-β-1 and of an active form of TGF-β-1. It is concluded that wine polyphenols increase total TGF-β-1 and have the potential to inhibit VSMC proliferation.

TABLE 9

Effect of wine and red wine polyphenols on plasma polyphenols and total TGFβ/two methods of assay

| Supplement | No | Polyphenols mg/g protein | Total TGF-β ng/ml Method 1 | Method 2 |
|---|---|---|---|---|
| Red wine | 8 | | | |
| Baseline | | 16.2 ± 1.87 | 6.6 ± 1.3 | 5.0 ± 0.4 |
| After 2 weeks | | 22.6 ± 0.91 | 15.5 ± 3.1 | 6.5 ± 0.5 |
| Difference of means | | 6.33 ± 0.96 | 8.9 ± 1.8 | 1.5 ± 0.1 |
| P-value | | 0.002 | 0.01 | 0.01 |
| White wine | 8 | | | |
| Baseline | | 18.9 ± 1.67 | 9.7 ± 2.5 | 5.6 ± 0.6 |
| After 2 weeks | | 20.2 ± 0.91 | 11.9 ± 3.4 | 5.3 ± 0.6 |
| Difference of means | | 1.33 ± 0.76 | 2.2 ± 0.9 | 0.3 ± 0.1 |
| P-value | | 0.5 | 0.5 | 0.8 |
| Polyphenol capsules | 8 | | | |
| Baseline | | 21.0 ± 0.96 | 9.0 ± 2.3 | 6.0 ± 0.7 |
| After 2 weeks | | 26.9 ± 1.76 | 19.8 ± 3.9 | 8.5 ± 0.9 |
| Difference of means | | 5.86 ± 0.80 | 10.8 ± 1.6 | 2.5 ± 0.2 |
| P-value | | 0.02 | 0.01 | 0.01 |
| Polyphenol drink | 6 | | | |
| Baseline | | 21.6 ± 0.35 | 9.2 ± 1.1 | 5.0 ± 1.5 |
| After 2 weeks | | 23.6 ± 0.40 | 15.6 ± 2.4 | 9.9 ± 1.1 |
| Difference of means | | 2.05 ± 0.05 | 6.4 ± 1.3 | 4.9 ± 0.4 |
| P-value | | 0.03 | 0.03 | 0.03 |

Mean ± sem

The inventors have additionally found surprisingly that it is possible to prepare a polyphenol composition (e.g. from red wine) which when given orally to a human subject will inhibit platelet aggregation and stimulate fibrinolysis.

In particular it has been demonstrated that when a preparation of polyphenols obtained from red wine is administered orally to man there is a decrease in platelet aggregation when arachidonic acid, ADP, collagen, or thrombin are used as agonists. Furthermore consumption of the polyphenol preparation increases tPA activity in the plasma of the subject.

The dosage of polyphenol preparation is dependent on the degree of activity of the material but will be between 10 mg and 10 g per day. Where the composition comprises the total phenolic pool obtained from red wine the preferred dose in 0.1 to 4.0 g per day and more preferably 1 to 2 g, which is equivalent to 0.5 to 1.0 litre of red wine per day.

EXAMPLE 14

A red wine polyphenol composition was prepared as described previously (Example 1 above).

The diet of twelve healthy men aged 35 to 65 was supplemented with 2 g red wine polyphenols (as described in Example 3) or aspirin (75 mg) daily for two weeks.

Fasting citrated blood was collected as a baseline and at four hours and two weeks after commencement of the trial, as follows: blood was obtained from the antecubital vein, with the subject in the recumbent position, using minimal stasis, into a syringe containing 011M citrate (1:9 v/v to blood). Platelet-rich plasma (PRP) was prepared by centrifugation of blood at 250 g for 10 minutes. Most of the PRP was removed and the platelet-poor plasma (PPP) was then prepared by centrifuging the residual blood at 2,500 g for 15 minutes. The concentration of platelets in the PRP was determined in a cell counter (Minos STX, ABX Ltd, Montpellier, France). Samples with a platelet count outside the range 150,000 to 350,000 per $\mu$l were rejected. The PRP was allowed to rest for at least 30 minutes before commencement of the aggregation studies. The time between blood collection and platelet aggregation was never more than three hours.

Platelet aggregation was determined on the freshly prepared platelets using a PAP-4C aggregometer (BioData, Alpha Laboratories, Southampton, UK). A 200 $\mu$l sample of PRP was added to a siliconised cuvette and incubated at 37° C. for 3 minutes. Aggregation was induced by the addition of 20 $\mu$l of the agonist (one of the following: arachidonic acid at 455 $\mu$g/ml; 1.8 $\mu$mol/L; collagen at 43 $\mu$g/ml obtained from BioData; thrombin at 0.11 U/ml, obtained from Sigma, Poole, Dorset, UK; all are final concentrations in the aggregation mixture). The platelet suspension was stirred at 1,000 rpm at 37° C. for 5 minutes. Maximum aggregation (percent from baseline) was determined within this time. The value was a measure of the aggregatory potential of the platelets, a decrease indicating an anti-aggregatory response when comparing samples drawn before and after consumption of the test material. Statistical significance was assessed by paired the t-test.

The red wine polyphenol powder inhibited platelet aggregation either acutely or chronically as shown in Table 10. These effects are similar to but smaller than those observed with aspirin (75 mg per day), except for thrombin. In particular, the effect of the polyphenols on arachidonate-induced aggregation suggests an inhibition of platelet cyclo-oxygenase activity. These results suggested that the red wine polyphenols have aspirin-like-effects, although there is an additional inhibitory effect on thrombin-induced aggregation.

TABLE 10

Maximum platelet aggregation in volunteers given red wine polyphenols or aspirin (%). Mean (SEM)

| | Red wine polyphenols[a] (12)† | | | Aspirin[b] (7)† | | |
|---|---|---|---|---|---|---|
| Agonist | Baseline | 4 hours | 2 weeks | Baseline | 4 hours | 2 weeks |
| Arachidonic acid (455 $\mu$g/ml) | 82.3(1.1) | 78.7(0.8)* | 79.0(0.8)** | 69.2(10.1) | 28.6(11.2)* | 12.6(1.9)** |
| ADP (1.8 $\mu$mol/L) | 42.4(3.4) | 37.6(3.3) | 38.7(2.9) | 39.2(4.2) | 31.5(3.7) | 31.3(2.6)* |
| Collagen (43 $\mu$g/mL) | 54.2(8.8) | 59.2(8.0) | 47.3(9.2)** | 67.5(5.1) | 24.6(5.0)*** | 21.8(4.7)*** |
| Thrombin (0.11 U/mL) | 22.0(1.7) | 17.4(1.8)** | 16.2(2.2)* | 15.5(2.8) | 13.9(4.5) | 12.2(2.0) |

*$P < 0.05$; $P < 0.01$ *$P < 0.001$ (difference from baseline)
†subjects [a]2 g/day [b]75 mg/day The same trial was used to investigate levels of PAI-1 and tPA activity in the subjects. Blood was obtained from the antecubital vein, with the subject in the recumbent position using minimal stasis, into a syringe containing 0.5M citrate, pH4.3 (Stabilyte™, 1:9 v/v to blood). Plasma was prepared by centrifugation of blood at 2,500 g for 15 minutes at 4° C., and frozen at −70° C. immediately.

All three samples (baseline, 4 hours and 2 weeks) from a subject were quickly thawed at 37° C. on the day of assay. tPA activities were determined using a commercially available kit (Chromolize™, from Biopool, Umea, Sweden) which is a bio-functional immunosorbent assay. Sample or standard (100 $\mu$l) was added to each well. The microtitre plate was incubated in a plate shaker for 20 minutes, after which time the contents of the wells were discarded, and the wells washed 4 times. Next, 50 $\mu$l of substrate solution was added to each well, followed by 50 $\mu$l of plasminogen reagent, and the plate incubated for a further 90 minutes. Finally, 50 $\mu$l of 1.7M glacial acetic acid solution was added to each well and mixed for 15 seconds. Absorbances were measured at 405 nm, and the activity of tPA in the sample read from a linear calibration curve. The significance of the differences between baseline, 4 hour and 2 week values for each treatment was assessed by a two-tailed paired t-test. The results are shown in Table 11.

The enzyme tPA constitutes an important protein in the fibrinolytic pathway, and its activity is thought to play a major role in the fibrinolytic system. The physiological role of tPA is to activate plasminogen to plasmin, which degrades fibrin to soluble fibrin-degradation products. In the assay of tPA, the specific inhibitor PAI-1 is usually present in a large excess and must be prevented from quenching tPA activity. This is provided for by use of Stabilyte™ blood collection tubes, which provide mild acidification of the sample.

Because PAI-1 values are known to be subject to diurnal variation, an additional trial was carried out in which the same subjects were studied using water as a placebo, instead of red wine polyphenols. The results are shown in Table 12.

TABLE 11

PAI-1 and tPA after supplementation with red wine polyphenols (2 g/day). Mean ± SEM

|  | N | Baseline | 4 hours | 2 weeks |
|---|---|---|---|---|
| PAI-1 antigen (ng/ml)6 |  | 18.8 ± 3.6 | 8.6 ± 1.0* | 17.0 ± 3.4 |
| tPA activity (IU/ml) | 10 | 0.62 ± 0.16 | 1.61 ± 0.30** | 0.71 ± 0.20 |

*P < 0.05  **P < 0.01 (difference from baseline)

TABLE 12

Comparison of 2 g red wine polyphenols with water after 4 hrs.

| Dose | Water | | Red wine polyphenols (2 g) | |
|---|---|---|---|---|
| Time | 0 hour | 4 hour | 0 hour | 4 hour |
| PAI-I Antigen (ng/ml) (n = 11) | | | | |
| Mean | 21.9 | 10.6 | 20.3 | 9.5 |
| SD | 12.7 | 4.2 | 9.0 | 3.1 |
| SEM | 3.8 | 1.3 | 2.7 | 0.9 |
| P value |  | 0.0061 |  | 0.0007 |
| tPA activity (IU/ml)(n = 9) | | | | |
| Mean | 0.821 | 1.221 | 0.566 | 1.511 |
| SD | 0.693 | 0.605 | 0.492 | 0.934 |
| SEM | 0.231 | 0.202 | 0.164 | 0.311 |
| P value |  | 0.1968 |  | 0.0136 |

Red wine polyphenols (2 g/day) produced a significant decrease in PAI-1 after 4 hours which was associated with a significant increase in tPA activity (Table 11). No changes were seen after an overnight fast after 2 weeks' treatment. However, as shown in Table 12, after 4 hours PAI-1 antigen concentration is decreased after administration of water, indicating that the effects on PAI-1 antigen concentration observed following polyphenol powder consumption were simply due to diurnal variation. Administration of water did not significantly increase tPA activity however, whilst red wine polyphenol powder gave a 2.7 fold increase in tPA activity. It is concluded that red wine polyphenols produce a beneficial effect in stimulating fibrinolysis by increasing tPA activity, but have no effect on PAI-1 antigen concentration. tPA promotes the formation of plasmin from plasminogen and plasmin converts the latent form of TGF-$\beta$ into its active form which then inhibits the growth of vascular smooth muscle cells (VSMC) which contribute to the growth of atherosclerotic plaques.

Preferably consumption of a composition in accordance with the invention will cause at least a 2% reduction in maximum platelet aggregation (as determined by the method described above) and/or an increase in tPA activity of at least 0.75 IU/ml (as determined by the method described above).

References

Assoian & Sporn (1986) J Cell Biol. 102, 1712–1733
Aznar et al Brit. Heart J. (1986) 59, 535–541
Bjorkerud (1991) Arteriosclerosis Thromb. 11, 892–902
Bradford (1976) Anal Biochem 72, 248–54
de Rijke et al (1996) Am. J. Clin. Nutr. 63, 329–34
Elwood et al (1991) Circulation 83, 38–44
Esterbauer et al (1989) Free Radic. Res. Commun. 6, 67–75
Francis, Am. Heart J. (1988) 115, 776–780
Frankel et al (1993) Lancet 341, 454–457
Frankel et al (1995) J. Agriculture and Food Chem. 43, 890–894
Fuhrman et al (1995) Am. J. Clin. Nutr. 61, 549–554
Goldberg (1995) Clin. Chem. 41, 14–16
Gorog et al (1994) Atherosclerosis 111, 47–53
Grainger et al (1995) Nature Medicine 1, 74–79
Gronbaek et al (1995) Brit Med J. 310, 1165–1169
Hamsten et al New Eng. J. Med. (1985) 313, 1557–1563
Hamsten et al Brit. Heart J. (1986) 55, 58–66
Hamsten et al Lancet, (1987) II, 3–9
Johnson, Int. J. Cardiol., (1984) 6, 380–382
Kirschenlohr et al (1993) Am. J Physiol. 265 (Cell Physiol. 34), C571–C576
Klatsky & Armstrong (1993) Amer. J.Cardiol. 71, 467–469
Lyons et al (1990) J.Cell Biol. 110, 1361–7
Massague, (1990) Annual Rev. Cell. Biol. 6, 597–641
McLoone et al (1995) Proc. Nutr. Soc. 54, Abstract 168A
Meade, (1987) in Thrombosis and Haemostasis, Verstraete et al (Eds.) Int. Soc. on
Thrombosis and Haemostasis Univ. Press Leuven, 37–60
Mehta et al J. Am. Coll. Cardiol., (1987) 9, 26
Moncada & Vane, New Eng. J. Med. (1979) 300, 1142–47
Olofsson et al Eur. Heart J. (1989) 10, 77–82
Owens et al (1988) J. Cell Biol. 107, 771–780
Paramo et al, Brit. Med. J. (1985) 291, 575–576
Price et al. (1995) Am. J. Enol. Viticulture, 46, 187–94
Renaud & De Lorgeril (1992) Lancet 339, 1523–1526
Shahidi & Nazck (1995) in Food phenolics, sources chemistry effects and applications
Technomic Publishing Co. Lancaster, USA p136–146
Sharpe et al., Q. J. Med. (1995) 88, 101–108
Singleton & Rossi (1965) Amer. J. Enology and Viticuture 16, 144–158
Steinberg, (1993) J. Intern. Med. 233, 227–232
St Leger et al (1979) Lancet 1, 1017–1020
Thaulou et al (1991) Circulation 84, 613–17

What is claimed is:

1. A method of providing a therapeutic effect in relation to the prevention or treatment of coronary heart disease in a subject, the method comprising providing a flavonol and anthocyanin containing dry composition prepared from plant-derived material selected from the group consisting of wine and grape juice, wherein the composition is water soluble and comprises at least 25% w/w polyphenols, the composition comprising at least 0.1% flavonol, and administering the composition to the subject in a therapeutically effective dosage.

2. A method according to claim 1, wherein said plant derived material is derived from wine.

3. A method according to claim 1, wherein said plant derived material is derived from grape juice.

4. A method according to claim 2, wherein said at least 25% polyphenols comprises the total polyphenol pool of red wine.

5. A method according to claim 1, wherein said composition further comprises an excipient, diluent or carrier.

6. A method according to claim 1, wherein said composition further comprises one or more substances selected from the group consisting of: nutrients, antioxidants, therapeutic substances, flavourings, and sweeteners.

7. A method according to claim 1, wherein said composition further comprises one or more substances selected from the group consisting of: lutein, lycopene, $\alpha$- or $\beta$-carotene, vitamin A, vitamin C, vitamin E ($\alpha$-tocopherol and other active tocopherols), folic acid, selenium, copper, zinc, manganese, ubiquinone (coenzyme Q10), salicylic acid, 2,3-dihydroxy benzoic acid, 2,5-dihydroxy benzoic acid, and aspirin.

8. A method according to claim 1, wherein said composition is packaged in unitary dose form.

9. A method according to claim 8, wherein said composition is in the form of a tablet, capsule or pill.

10. A method according to claim 1, wherein said composition is administered as a drink, said drink made by mixing said composition with a physiologically acceptable liquid.

11. A method according to claim 10, wherein said physiologically acceptable liquid is selected from the group consisting of water, an aqueous solution, an alcoholic solution, fruit juice, milk, yogurt, or aqueous solution of Aloe Vera.

12. A method of inhibiting oxidation of plasma LDL in a human subject, the method including providing a flavonol and anthocyanin containing dry composition prepared from plant-derived material selected from the group consisting of wine or grape juice, wherein the composition is water soluble and comprises at least 25% w/w polyphenols, the composition comprising at least 0.1% flavonol, and administering the composition to the subject in a therapeutically effective dosage.

13. A method according to claim 12, wherein said plant derived material is derived from wine.

14. A method according to claim 12, wherein said plant derived material is derived from grape juice.

15. A method according to claim 13, wherein said at least 25% polyphenols comprises the total polyphenol pool of red wine.

16. A method according to claim 12, wherein said composition further comprises an excipient, diluent or carrier.

17. A method according to claim 12, wherein said composition further comprises one or more substances selected from the group consisting of: nutrients, antioxidants, therapeutic substances, flavourings, and sweeteners.

18. A method according to claim 12, wherein said composition further comprises one or more substances selected from the group consisting of: lutein, lycopene, $\alpha$- or $\beta$-carotene, vitamin A, vitamin C, vitamin E ($\alpha$-tocopherol and other active tocopherols), folic acid, selenium, copper, zinc, manganese, ubiquinone (coenzyme Q10), salicylic acid, 2,3-dihydroxy benzoic acid, 2,5-dihydroxy benzoic acid, and aspirin.

19. A method according to claim 12, wherein said composition is packaged in unitary dose form.

20. A method according to claim 19, wherein said composition is in the form of a tablet, capsule or pill.

21. A method according to claim 12, wherein said composition is administered as a drink, said drink made by mixing said composition with a physiologically acceptable liquid.

22. A method according to claim 21, wherein said physiologically acceptable liquid is selected from the group consisting of water, an aqueous solution, an alcoholic solution, fruit juice, milk, yogurt, or aqueous solution of Aloe Vera.

23. A method of stimulating TGF-$\beta$ production in a human subject, the method including providing a flavonol and anthocyanin containing dry composition prepared from plant-derived material selected from the group consisting of wine or grape juice, wherein the composition is water soluble and comprises at least 25% w/w polyphenols, the composition comprising at least 0.1% flavonol, and administering the composition to the subject in a therapeutically effective dosage.

24. A method according to claim 23, wherein said plant derived material is derived from wine.

25. A method according to claim 23, wherein said plant derived material is derived from grape juice.

26. A method according to claim 24, wherein said at least 25% polyphenols comprises the total polyphenol pool of red wine.

27. A method according to claim 23, wherein said composition further comprises an excipient, diluent or carrier.

28. A method according to claim 23, wherein said composition further comprises one or more substances selected from the group consisting of: nutrients, antioxidants, therapeutic substances, flavourings, and sweeteners.

29. A method according to claim 23, wherein said composition further comprises one or more substances selected from the group consisting of: lutein, lycopene, $\alpha$- or $\gamma$-carotene, vitamin A, vitamin C, vitamin E ($\alpha$-tocopherol and other active tocopherols), folic acid, selenium, copper, zinc, manganese, ubiquinone (coenzyme Q10), salicylic acid, 2,3-dihydroxy benzoic acid, 2,5-dihydroxy benzoic acid, and aspirin.

30. A method according to claim 23, wherein said composition is packaged in unitary dose form.

31. A method according to claim 30, wherein said composition is in the form of a tablet, capsule or pill.

32. A method according to claim 23, wherein said composition is administered as a drink, said drink made by mixing said composition with a physiologically acceptable liquid.

33. A method according to claim 32, wherein said physiologically acceptable liquid is selected from the group consisting of water, an aqueous solution, an alcoholic solution, fruit juice, milk, yogurt, or aqueous solution of Aloe Vera.

34. A method of inhibiting platelet aggregation or stimulating fibrinolysis in a human subject, the method including providing a flavonol and anthocyanin containing dry composition prepared from plant-derived material selected from the group consisting of wine and grape juice, wherein the composition is water soluble and comprises at least 25% w/w polyphenols, the composition comprising at least 0.1% flavonol, and administering the composition to the subject in a therapeutically effective dosage.

35. A method according to claim 34, wherein said plant derived material is derived from wine.

36. A method according to claim 34, wherein said plant derived material is derived from grape juice.

37. A method according to claim 35, wherein said at least 25% polyphenols comprises the total polyphenol pool of red wine.

38. A method according to claim 34, wherein said composition further comprises an excipient, diluent or carrier.

39. A method according to claim 34, wherein said composition further comprises one or more substances selected from the group consisting of: nutrients, antioxidants, therapeutic substances, flavourings, and sweeteners.

40. A method according to claim 34, wherein said composition further comprises one or more substances selected from the group consisting of: lutein, lycopene, $\alpha$- or $\beta$-carotene, vitamin A, vitamin C, vitamin E ($\alpha$-tocopherol and other active tocopherols), folic acid, selenium, copper, zinc, manganese, ubiquinone (coenzyme Q10), salicylic acid, 2,3-dihydroxy benzoic acid, 2,5-dihydroxy benzoic acid, and aspirin.

41. A method according to claim 34, wherein said composition is packaged in unitary dose form.

42. A method according to claim 41, wherein said composition is in the form of a tablet, capsule or pill.

43. A method according to claim 34, wherein said composition is administered as a drink, said drink made by mixing said composition with a physiologically acceptable liquid.

44. A method according to claim 43, wherein said physiologically acceptable liquid is selected from the group consisting of water, an aqueous solution, an alcoholic solution, fruit juice, milk, yogurt, or aqueous solution of Aloe Vera.

* * * * *